United States Patent
Anvar et al.

(10) Patent No.: US 12,419,738 B2
(45) Date of Patent: Sep. 23, 2025

(54) FLUID FOR ACCOMMODATING INTRAOCULAR LENSES

(71) Applicant: Alcon Inc., Fribourg (CH)

(72) Inventors: David J. Anvar, Sunnyvale, CA (US); Andrew Goodwin, San Leandro, CA (US); David Chazan, Palo Alto, CA (US)

(73) Assignee: Alcon Inc., Fribourg (CH)

( * ) Notice: Subject to any disclaimer, the term of this patent is extended or adjusted under 35 U.S.C. 154(b) by 89 days.

(21) Appl. No.: 18/348,696

(22) Filed: Jul. 7, 2023

(65) Prior Publication Data

US 2023/0355375 A1    Nov. 9, 2023

Related U.S. Application Data

(60) Division of application No. 17/200,047, filed on Mar. 12, 2021, now Pat. No. 11,737,862, which is a continuation of application No. 14/555,001, filed on Nov. 26, 2014, now Pat. No. 10,980,629, which is a continuation of application No. 13/033,474, filed on Feb. 23, 2011, now Pat. No. 8,900,298.

(60) Provisional application No. 61/307,354, filed on Feb. 23, 2010.

(51) Int. Cl.
| | |
|---|---|
| A61F 2/00 | (2006.01) |
| A61F 2/16 | (2006.01) |
| A61L 27/14 | (2006.01) |
| A61L 27/50 | (2006.01) |
| C07F 7/18 | (2006.01) |
| C07F 7/20 | (2006.01) |
| C08G 77/34 | (2006.01) |
| C08G 77/00 | (2006.01) |
| C08L 83/04 | (2006.01) |

(52) U.S. Cl.
CPC ............ *A61F 2/1613* (2013.01); *A61L 27/14* (2013.01); *A61L 27/50* (2013.01); *C07F 7/1804* (2013.01); *C07F 7/20* (2013.01); *C08G 77/34* (2013.01); *C08G 77/80* (2013.01); *C08L 83/04* (2013.01)

(58) Field of Classification Search
None
See application file for complete search history.

(56) References Cited

U.S. PATENT DOCUMENTS

| | | |
|---|---|---|
| 2,990,670 A | 7/1961 | Kingsbury |
| 3,915,172 A | 10/1975 | Wichterle et al. |
| 4,253,199 A | 3/1981 | Banko |
| 4,273,109 A | 6/1981 | Enderby |
| 4,298,996 A | 11/1981 | Barnet |
| 4,304,895 A | 12/1981 | Loshaek |
| 4,423,809 A | 1/1984 | Mazzocco |
| 4,435,855 A | 3/1984 | Pannu |
| 4,461,294 A | 7/1984 | Baron |
| 4,466,705 A | 8/1984 | Michelson |
| 4,490,860 A | 1/1985 | Rainin |
| 4,494,254 A | 1/1985 | Lopez |
| 4,512,040 A | 4/1985 | Mcclure |
| 4,528,311 A | 7/1985 | Beard et al. |
| 4,538,608 A | 9/1985 | L'Esperance |
| 4,558,698 A | 12/1985 | O'Dell |
| 4,566,438 A | 1/1986 | Liese et al. |
| 4,604,087 A | 8/1986 | Joseph |
| 4,617,715 A | 10/1986 | Koistinen et al. |
| 4,633,866 A | 1/1987 | Peyman et al. |
| 4,634,418 A | 1/1987 | Binder |
| 4,685,921 A | 8/1987 | Peyman |
| 4,685,922 A | 8/1987 | Peyman |
| 4,693,717 A | 9/1987 | Michelson |
| 4,722,724 A | 2/1988 | Schocket |
| 4,729,373 A | 3/1988 | Peyman |
| 4,731,079 A | 3/1988 | Stoy |
| 4,750,901 A | 6/1988 | Molteno |
| 4,770,654 A | 9/1988 | Rogers et al. |
| 4,781,719 A | 11/1988 | Kelman |
| 4,784,485 A | 11/1988 | Ho |
| 4,819,631 A | 4/1989 | Poley |
| 4,842,601 A | 6/1989 | Smith |
| 4,848,343 A | 7/1989 | Wallsten et al. |
| 4,861,341 A | 8/1989 | Woodburn |
| 4,863,457 A | 9/1989 | Lee |
| 4,876,250 A | 10/1989 | Clark |
| 4,880,000 A | 11/1989 | Holmes et al. |
| 4,902,293 A | 2/1990 | Feaster |
| 4,906,247 A | 3/1990 | Fritch |
| 4,911,714 A | 3/1990 | Poley |
| 4,934,363 A | 6/1990 | Smith et al. |
| 4,934,809 A | 6/1990 | Volk |
| 4,946,436 A | 8/1990 | Smith |
| 4,963,148 A | 10/1990 | Sulc et al. |
| 4,994,060 A | 2/1991 | Rink et al. |
| 4,995,880 A | 2/1991 | Galib |
| 5,007,510 A | 4/1991 | Houng |
| 5,035,710 A | 7/1991 | Nakada et al. |
| 5,041,081 A | 8/1991 | Odrich |
| 5,047,051 A | 9/1991 | Cumming |

(Continued)

FOREIGN PATENT DOCUMENTS

| | | |
|---|---|---|
| CN | 1283974 | 2/2001 |
| CN | 1367667 | 9/2002 |

(Continued)

OTHER PUBLICATIONS

CN-100471898-C-English translation (Year: 2009).*

(Continued)

*Primary Examiner* — Stefanie J Cohen

(74) *Attorney, Agent, or Firm* — Levine Bagade Han LLP

(57) ABSTRACT

Fluids incorporated into intraocular lenses and their methods of use. In some embodiments the fluids are silicone oils, and in some embodiments they are used in accommodating intraocular lenses.

12 Claims, No Drawings

(56) References Cited

U.S. PATENT DOCUMENTS

| | | | |
|---|---|---|---|
| 5,066,301 A | 11/1991 | Wiley | |
| 5,100,410 A | 3/1992 | Dulebohn | |
| 5,108,429 A | 4/1992 | Wiley | |
| 5,123,902 A | 6/1992 | Muller et al. | |
| 5,127,901 A | 7/1992 | Odrich | |
| 5,145,935 A | 9/1992 | Hayashi | |
| 5,152,789 A | 10/1992 | Willis | |
| 5,169,920 A * | 12/1992 | Okawa | C08G 77/06 528/33 |
| 5,171,241 A | 12/1992 | Buboltz et al. | |
| 5,171,266 A | 12/1992 | Wiley et al. | |
| 5,180,362 A | 1/1993 | Worst | |
| 5,235,003 A | 8/1993 | Ward et al. | |
| 5,238,004 A | 8/1993 | Sahatjian et al. | |
| 5,246,452 A | 9/1993 | Sinnott | |
| 5,251,993 A | 10/1993 | Sigourney | |
| 5,254,112 A | 10/1993 | Sinofsky et al. | |
| 5,275,624 A | 1/1994 | Hara et al. | |
| 5,304,182 A | 4/1994 | Rheinish et al. | |
| 5,326,347 A | 7/1994 | Cumming | |
| 5,354,333 A | 10/1994 | Kammann et al. | |
| 5,360,399 A | 11/1994 | Stegmann | |
| 5,372,577 A | 12/1994 | Ungerleider | |
| 5,391,590 A | 2/1995 | Gerace et al. | |
| 5,426,166 A | 6/1995 | Usifer et al. | |
| 5,433,701 A | 7/1995 | Rubinstein | |
| 5,443,505 A | 8/1995 | Wong et al. | |
| 5,444,135 A | 8/1995 | Cheradame et al. | |
| 5,445,637 A | 8/1995 | Bretton | |
| 5,454,746 A | 10/1995 | Guegan et al. | |
| 5,454,796 A | 10/1995 | Krupin | |
| 5,468,246 A | 11/1995 | Blake | |
| 5,489,302 A | 2/1996 | Skottun | |
| 5,549,614 A | 8/1996 | Tunis | |
| 5,558,630 A | 9/1996 | Fisher | |
| 5,562,676 A | 10/1996 | Brady et al. | |
| 5,578,081 A | 11/1996 | Mcdonald | |
| 5,585,049 A | 12/1996 | Grisoni et al. | |
| 5,591,223 A | 1/1997 | Lock et al. | |
| 5,593,436 A | 1/1997 | Langerman | |
| 5,626,559 A | 5/1997 | Solomon | |
| 5,628,795 A | 5/1997 | Langerman | |
| 5,633,504 A | 5/1997 | Collins et al. | |
| 5,651,782 A | 7/1997 | Simon et al. | |
| 5,653,753 A | 8/1997 | Brady et al. | |
| 5,676,669 A | 10/1997 | Colvard | |
| 5,676,944 A | 10/1997 | Alvarado et al. | |
| 5,684,637 A | 11/1997 | Floyd | |
| 5,702,414 A | 12/1997 | Richter et al. | |
| 5,713,844 A | 2/1998 | Peyman | |
| 5,735,858 A | 4/1998 | Makker et al. | |
| 5,738,677 A | 4/1998 | Colvard et al. | |
| 5,741,292 A | 4/1998 | Mendius | |
| 5,767,669 A | 6/1998 | Hansen et al. | |
| 5,776,138 A | 7/1998 | Vidal et al. | |
| 5,792,099 A | 8/1998 | Decamp et al. | |
| 5,803,925 A | 9/1998 | Yang et al. | |
| 5,807,244 A | 9/1998 | Barot | |
| 5,807,302 A | 9/1998 | Wandel | |
| 5,868,697 A | 2/1999 | Richter et al. | |
| 5,868,751 A | 2/1999 | Feingold | |
| 5,873,879 A | 2/1999 | Figueroa et al. | |
| RE36,150 E | 3/1999 | Gupta | |
| 5,885,279 A | 3/1999 | Bretton | |
| 5,919,171 A | 7/1999 | Kira et al. | |
| 5,993,438 A | 11/1999 | Juhasz et al. | |
| 6,001,107 A | 12/1999 | Feingold | |
| 6,002,480 A | 12/1999 | Izatt et al. | |
| 6,036,678 A | 3/2000 | Giungo | |
| 6,048,348 A | 4/2000 | Chambers et al. | |
| 6,050,999 A | 4/2000 | Paraschac et al. | |
| 6,102,045 A | 8/2000 | Nordquist et al. | |
| 6,146,375 A | 11/2000 | Juhasz et al. | |
| 6,152,918 A | 11/2000 | Padilla et al. | |
| 6,188,526 B1 | 2/2001 | Sasaya et al. | |
| 6,203,513 B1 | 3/2001 | Yaron et al. | |
| 6,214,961 B1 * | 4/2001 | Aoki | C08G 77/04 528/21 |
| 6,225,367 B1 | 5/2001 | Chaouk et al. | |
| 6,229,641 B1 | 5/2001 | Kosaka | |
| 6,238,409 B1 | 5/2001 | Hojeibane | |
| 6,251,090 B1 | 6/2001 | Avery et al. | |
| 6,283,975 B1 | 9/2001 | Glick et al. | |
| 6,283,976 B1 | 9/2001 | Portney | |
| 6,336,932 B1 | 1/2002 | Figueroa et al. | |
| 6,342,073 B1 | 1/2002 | Cumming et al. | |
| 6,387,101 B1 | 5/2002 | Butts et al. | |
| 6,398,789 B1 | 6/2002 | Capetan | |
| 6,406,481 B2 | 6/2002 | Feingold et al. | |
| 6,406,494 B1 | 6/2002 | Laguette et al. | |
| 6,436,092 B1 | 8/2002 | Peyman | |
| 6,464,724 B1 | 10/2002 | Lynch et al. | |
| 6,464,725 B2 | 10/2002 | Skotton | |
| 6,488,708 B2 | 12/2002 | Sarfarazi | |
| 6,491,697 B1 | 12/2002 | Clark et al. | |
| 6,497,708 B1 | 12/2002 | Cumming | |
| 6,503,275 B1 | 1/2003 | Cumming | |
| 6,508,779 B1 | 1/2003 | Suson | |
| 6,508,803 B1 | 1/2003 | Horikawa et al. | |
| 6,510,600 B2 | 1/2003 | Yaron et al. | |
| 6,517,577 B1 | 2/2003 | Callahan et al. | |
| 6,533,768 B1 | 3/2003 | Hill | |
| 6,537,283 B2 | 3/2003 | Van Noy | |
| 6,552,860 B1 | 4/2003 | Alden | |
| 6,585,768 B2 | 7/2003 | Hamano et al. | |
| 6,599,317 B1 | 7/2003 | Weinschenk et al. | |
| 6,601,956 B1 | 8/2003 | Jean et al. | |
| 6,605,093 B1 | 8/2003 | Blake | |
| 6,610,350 B2 | 8/2003 | Suzuki et al. | |
| 6,616,691 B1 | 9/2003 | Tran | |
| 6,616,692 B1 | 9/2003 | Glick et al. | |
| 6,626,858 B2 | 9/2003 | Lynch et al. | |
| 6,638,239 B1 | 10/2003 | Bergheim et al. | |
| 6,638,306 B2 | 10/2003 | Cumming | |
| 6,645,245 B1 | 11/2003 | Preussner | |
| 6,660,035 B1 | 12/2003 | Lang et al. | |
| 6,676,607 B2 | 1/2004 | De Juan et al. | |
| 6,699,210 B2 | 3/2004 | Williams et al. | |
| 6,699,211 B2 | 3/2004 | Savage | |
| 6,709,108 B2 | 3/2004 | Levine et al. | |
| 6,712,848 B1 | 3/2004 | Wolf et al. | |
| 6,730,056 B1 | 5/2004 | Ghaem et al. | |
| 6,730,123 B1 | 5/2004 | Klopotek | |
| 6,783,544 B2 | 8/2004 | Lynch et al. | |
| 6,818,158 B2 | 11/2004 | Pham et al. | |
| 6,827,699 B2 | 12/2004 | Lynch et al. | |
| 6,827,738 B2 | 12/2004 | Willis et al. | |
| 6,860,601 B2 | 3/2005 | Shadduck | |
| 6,881,198 B2 | 4/2005 | Brown | |
| 6,881,225 B2 | 4/2005 | Okada | |
| 6,914,247 B2 | 7/2005 | Duggan et al. | |
| 6,923,815 B2 | 8/2005 | Brady et al. | |
| 6,926,736 B2 | 8/2005 | Peng et al. | |
| 6,949,093 B1 | 9/2005 | Peyman | |
| 6,969,403 B2 | 11/2005 | Peng et al. | |
| 6,981,958 B1 | 1/2006 | Gharib et al. | |
| 7,001,374 B2 | 2/2006 | Peyman | |
| 7,147,650 B2 | 12/2006 | Lee | |
| 7,156,854 B2 | 1/2007 | Brown et al. | |
| 7,297,130 B2 | 11/2007 | Bergheim et al. | |
| 7,311,194 B2 | 12/2007 | Jin et al. | |
| 7,331,984 B2 | 2/2008 | Tu et al. | |
| 7,438,723 B2 | 10/2008 | Esch | |
| 7,615,073 B2 | 11/2009 | Deacon et al. | |
| 7,637,947 B2 | 12/2009 | Smith et al. | |
| 7,867,186 B2 | 1/2011 | Haffner et al. | |
| 7,867,205 B2 | 1/2011 | Bergheim et al. | |
| 7,988,290 B2 | 8/2011 | Campbell et al. | |
| 8,012,115 B2 | 9/2011 | Karageozian | |
| 8,052,752 B2 | 11/2011 | Woods et al. | |
| 8,308,701 B2 | 11/2012 | Horvath et al. | |
| 8,480,734 B2 | 7/2013 | Kellan et al. | |
| 8,540,659 B2 | 9/2013 | Berlin | |
| 8,551,166 B2 | 10/2013 | Schieber et al. | |

(56) References Cited

U.S. PATENT DOCUMENTS

| | | |
|---|---|---|
| 8,613,766 B2 | 12/2013 | Richardson et al. |
| 8,641,748 B2 | 2/2014 | Hebert et al. |
| 8,647,659 B2 | 2/2014 | Robinson et al. |
| 8,657,776 B2 | 2/2014 | Wardle et al. |
| 8,758,361 B2 | 6/2014 | Kobayashi et al. |
| 8,888,845 B2 | 11/2014 | Vaquero et al. |
| 8,900,298 B2 | 12/2014 | Anvar et al. |
| 8,961,447 B2 | 2/2015 | Schieber et al. |
| 8,968,328 B2 | 3/2015 | Ichinohe et al. |
| 8,974,511 B2 | 3/2015 | Horvath et al. |
| 8,992,609 B2 | 3/2015 | Shadduck |
| 9,039,650 B2 | 5/2015 | Schieber et al. |
| 9,066,783 B2 | 6/2015 | Euteneuer et al. |
| 9,155,655 B2 | 10/2015 | Schieber et al. |
| 9,226,852 B2 | 1/2016 | Schieber et al. |
| 9,277,987 B2 | 3/2016 | Smiley et al. |
| 9,326,846 B2 | 5/2016 | Devita Gerardi et al. |
| 9,329,306 B2 | 5/2016 | Huang et al. |
| 9,351,874 B2 | 5/2016 | Schieber et al. |
| 9,358,156 B2 | 6/2016 | Wardle et al. |
| 9,579,234 B2 | 2/2017 | Wardle et al. |
| 9,603,741 B2 | 3/2017 | Berlin |
| 9,610,155 B2 | 4/2017 | Matthews |
| 9,693,901 B2 | 7/2017 | Horvath et al. |
| 9,795,473 B2 | 10/2017 | Smiley et al. |
| 9,872,763 B2 | 1/2018 | Smiley et al. |
| 10,159,566 B2 | 12/2018 | Hadba et al. |
| 10,195,020 B2 | 2/2019 | Matthews |
| 10,299,913 B2 | 5/2019 | Smiley et al. |
| 10,335,314 B2 | 7/2019 | Berlin |
| 10,357,356 B2 | 7/2019 | Smiley et al. |
| 10,406,025 B2 | 9/2019 | Wardle et al. |
| 10,492,949 B2 | 12/2019 | Wardle et al. |
| 10,534,113 B2 | 1/2020 | Shadduck |
| 10,617,558 B2 | 4/2020 | Schieber et al. |
| 11,426,270 B2 | 8/2022 | Hildebrand et al. |
| 2002/0003546 A1 | 1/2002 | Mochimaru et al. |
| 2002/0010278 A1* | 1/2002 | Garcia-Franco ...... C08F 257/02 526/348.3 |
| 2002/0013553 A1 | 1/2002 | Pajunk et al. |
| 2002/0055776 A1 | 5/2002 | Juan et al. |
| 2002/0072673 A1 | 6/2002 | Yamamoto et al. |
| 2002/0072795 A1 | 6/2002 | Green |
| 2002/0095212 A1 | 7/2002 | Boehm |
| 2002/0107568 A1 | 8/2002 | Zadno-Azizi et al. |
| 2002/0161434 A1 | 10/2002 | Laguette et al. |
| 2002/0193876 A1 | 12/2002 | Lang et al. |
| 2003/0014092 A1 | 1/2003 | Neuhann |
| 2003/0018384 A1 | 1/2003 | Valyunin et al. |
| 2003/0040754 A1 | 2/2003 | Mitchell et al. |
| 2003/0060878 A1 | 3/2003 | Shadduck |
| 2003/0078657 A1 | 4/2003 | Zadno-Azizi et al. |
| 2003/0109926 A1 | 6/2003 | Portney |
| 2003/0120200 A1 | 6/2003 | Bergheim |
| 2003/0125351 A1 | 7/2003 | Azuma et al. |
| 2003/0135272 A1 | 7/2003 | Brady et al. |
| 2003/0149480 A1 | 8/2003 | Shadduck |
| 2003/0180522 A1 | 9/2003 | DeSimone et al. |
| 2003/0181848 A1 | 9/2003 | Bergheim et al. |
| 2003/0183960 A1 | 10/2003 | Buazza et al. |
| 2003/0187384 A1 | 10/2003 | Bergheim |
| 2003/0199977 A1 | 10/2003 | Cumming |
| 2003/0229303 A1 | 12/2003 | Haffner et al. |
| 2004/0001180 A1 | 1/2004 | Epstein |
| 2004/0015236 A1 | 1/2004 | Sarfarazi |
| 2004/0024345 A1 | 2/2004 | Gharib et al. |
| 2004/0024453 A1 | 2/2004 | Castillejos |
| 2004/0059343 A1 | 3/2004 | Shearer et al. |
| 2004/0066489 A1 | 4/2004 | Benedikt et al. |
| 2004/0073156 A1 | 4/2004 | Brown |
| 2004/0082939 A1 | 4/2004 | Berlin |
| 2004/0082994 A1 | 4/2004 | Woods et al. |
| 2004/0088048 A1 | 5/2004 | Richter et al. |
| 2004/0088050 A1 | 5/2004 | Norrby et al. |
| 2004/0092856 A1 | 5/2004 | Dahan |
| 2004/0098124 A1 | 5/2004 | Freeman et al. |
| 2004/0106975 A1 | 6/2004 | Solovay et al. |
| 2004/0111152 A1 | 6/2004 | Kelman |
| 2004/0122380 A1 | 6/2004 | Utterberg |
| 2004/0127843 A1 | 7/2004 | Tu et al. |
| 2004/0127984 A1 | 7/2004 | Paul et al. |
| 2004/0147870 A1 | 7/2004 | Burns et al. |
| 2004/0181279 A1 | 9/2004 | Nun |
| 2004/0210185 A1 | 10/2004 | Tu et al. |
| 2004/0225357 A1 | 11/2004 | Worst et al. |
| 2004/0228013 A1 | 11/2004 | Goldstein et al. |
| 2004/0230203 A1 | 11/2004 | Yaguchi |
| 2004/0249333 A1 | 12/2004 | Bergheim |
| 2004/0254520 A1 | 12/2004 | Porteous et al. |
| 2004/0254521 A1 | 12/2004 | Simon |
| 2004/0267359 A1 | 12/2004 | Makker et al. |
| 2005/0021139 A1 | 1/2005 | Shadduck |
| 2005/0033308 A1 | 2/2005 | Callahan et al. |
| 2005/0041200 A1 | 2/2005 | Rich |
| 2005/0049578 A1 | 3/2005 | Tu et al. |
| 2005/0060016 A1 | 3/2005 | Wu et al. |
| 2005/0090807 A1 | 4/2005 | Lynch et al. |
| 2005/0101967 A1 | 5/2005 | Weber et al. |
| 2005/0107734 A1 | 5/2005 | Coroneo |
| 2005/0113911 A1 | 5/2005 | Peyman |
| 2005/0125003 A1 | 6/2005 | Pinchuk et al. |
| 2005/0143750 A1 | 6/2005 | Vaquero |
| 2005/0146685 A1 | 7/2005 | Hanaki et al. |
| 2005/0147735 A1 | 7/2005 | Lowery et al. |
| 2005/0149183 A1 | 7/2005 | Shadduck |
| 2005/0154443 A1 | 7/2005 | Linder et al. |
| 2005/0191331 A1 | 9/2005 | Hunter et al. |
| 2005/0192527 A1 | 9/2005 | Gharib et al. |
| 2005/0197613 A1 | 9/2005 | Sniegowski et al. |
| 2005/0209549 A1 | 9/2005 | Bergheim |
| 2005/0222577 A1 | 10/2005 | Vaquero |
| 2005/0222579 A1 | 10/2005 | Vaquero et al. |
| 2005/0240168 A1 | 10/2005 | Neuberger et al. |
| 2005/0251253 A1 | 11/2005 | Gross |
| 2005/0251254 A1 | 11/2005 | Brady et al. |
| 2005/0255231 A1 | 11/2005 | Hill et al. |
| 2005/0266047 A1 | 12/2005 | Tu et al. |
| 2005/0283162 A1 | 12/2005 | Stratas |
| 2005/0288619 A1 | 12/2005 | Gharib et al. |
| 2006/0084907 A1 | 4/2006 | Bergheim |
| 2006/0116626 A1 | 6/2006 | Smedley et al. |
| 2006/0129129 A1 | 6/2006 | Smith |
| 2006/0129141 A1 | 6/2006 | Lin |
| 2006/0155265 A1 | 7/2006 | Juhasz et al. |
| 2006/0189915 A1 | 8/2006 | Camras et al. |
| 2007/0004886 A1 | 1/2007 | Schorzman et al. |
| 2007/0118147 A1 | 5/2007 | Smedley et al. |
| 2007/0129717 A1 | 6/2007 | Brown et al. |
| 2007/0191863 A1 | 8/2007 | De Juan et al. |
| 2007/0203578 A1 | 8/2007 | Scholl et al. |
| 2007/0213817 A1 | 9/2007 | Esch et al. |
| 2007/0219509 A1 | 9/2007 | Tashiro et al. |
| 2007/0260157 A1 | 11/2007 | Norrby |
| 2007/0276315 A1 | 11/2007 | Haffner et al. |
| 2007/0282245 A1 | 12/2007 | Tu et al. |
| 2007/0282438 A1 | 12/2007 | Hong et al. |
| 2007/0293872 A1 | 12/2007 | Peyman |
| 2007/0298068 A1 | 12/2007 | Badawi et al. |
| 2007/0299487 A1 | 12/2007 | Shadduck |
| 2008/0004699 A1 | 1/2008 | Ben Nun |
| 2008/0015488 A1 | 1/2008 | Tu et al. |
| 2008/0027537 A1 | 1/2008 | Gerlach et al. |
| 2008/0045878 A1 | 2/2008 | Bergheim |
| 2008/0065096 A1 | 3/2008 | Kappelhof et al. |
| 2008/0119827 A1 | 5/2008 | Kurtz et al. |
| 2008/0119865 A1 | 5/2008 | Meunier et al. |
| 2008/0125862 A1 | 5/2008 | Blake |
| 2008/0139769 A1 | 6/2008 | Iwamoto et al. |
| 2008/0200860 A1 | 8/2008 | Tu et al. |
| 2008/0200982 A1* | 8/2008 | Your ................ A61L 27/16 623/6.37 |
| 2008/0234624 A2 | 9/2008 | Bergheim et al. |
| 2008/0269887 A1 | 10/2008 | Cumming |
| 2008/0269987 A1 | 10/2008 | Barron et al. |

(56) References Cited

U.S. PATENT DOCUMENTS

| | | |
|---|---|---|
| 2008/0300680 A1 | 12/2008 | Joshua |
| 2008/0306587 A1 | 12/2008 | Your |
| 2008/0312661 A1 | 12/2008 | Downer et al. |
| 2009/0005852 A1 | 1/2009 | Gittings et al. |
| 2009/0005865 A1 | 1/2009 | Smiley et al. |
| 2009/0018512 A1 | 1/2009 | Charles |
| 2009/0030415 A1 | 1/2009 | Gogolewski |
| 2009/0030425 A1 | 1/2009 | Smiley et al. |
| 2009/0036819 A1 | 2/2009 | Tu et al. |
| 2009/0036840 A1 | 2/2009 | Viray et al. |
| 2009/0036898 A1 | 2/2009 | Ichinohe et al. |
| 2009/0043321 A1 | 2/2009 | Conston et al. |
| 2009/0076602 A1 | 3/2009 | Ho et al. |
| 2009/0079940 A1 | 3/2009 | Dai et al. |
| 2009/0082860 A1 | 3/2009 | Schieber et al. |
| 2009/0082863 A1 | 3/2009 | Schieber et al. |
| 2009/0112313 A1 | 4/2009 | Mentak |
| 2009/0118718 A1 | 5/2009 | Raksi et al. |
| 2009/0124773 A1 | 5/2009 | Zhou et al. |
| 2009/0171366 A1 | 7/2009 | Tanaka |
| 2009/0204053 A1 | 8/2009 | Nissan et al. |
| 2009/0204123 A1 | 8/2009 | Downer |
| 2009/0227934 A1 | 9/2009 | Euteneuer et al. |
| 2009/0228101 A1 | 9/2009 | Zadno-Azizi |
| 2009/0234449 A1* | 9/2009 | De Juan, Jr. .......... A61F 2/1635 623/6.22 |
| 2009/0259126 A1 | 10/2009 | Saal et al. |
| 2009/0270876 A1 | 10/2009 | Hoffmann et al. |
| 2009/0281520 A1 | 11/2009 | Highley et al. |
| 2009/0292293 A1 | 11/2009 | Bogaert et al. |
| 2009/0306774 A1 | 12/2009 | Park |
| 2009/0312836 A1 | 12/2009 | Pinchuk et al. |
| 2009/0318933 A1 | 12/2009 | Anderson |
| 2010/0010416 A1 | 1/2010 | Juan et al. |
| 2010/0063588 A1 | 3/2010 | Park |
| 2010/0069522 A1 | 3/2010 | Linhardt et al. |
| 2010/0094412 A1 | 4/2010 | Wensrich |
| 2010/0130985 A1 | 5/2010 | Tanaka |
| 2010/0137981 A1 | 6/2010 | Silvestrini et al. |
| 2010/0140114 A1* | 6/2010 | Pruitt .................... G02B 1/043 53/425 |
| 2010/0173866 A1 | 7/2010 | Hee et al. |
| 2010/0262174 A1 | 10/2010 | Sretavan et al. |
| 2011/0028950 A1 | 2/2011 | Raksi et al. |
| 2011/0118834 A1 | 5/2011 | Lo et al. |
| 2012/0035524 A1 | 2/2012 | Silvestrini |
| 2012/0296425 A1 | 11/2012 | Cumming |
| 2012/0323159 A1 | 12/2012 | Wardle et al. |
| 2013/0253437 A1 | 9/2013 | Badawi et al. |
| 2014/0012279 A1 | 1/2014 | De Juan et al. |
| 2014/0121584 A1 | 5/2014 | Wardle et al. |
| 2014/0214161 A1 | 7/2014 | Schieber et al. |
| 2014/0249625 A1 | 9/2014 | Shadduck |
| 2014/0257478 A1 | 9/2014 | Mccafferty |
| 2014/0330375 A1 | 11/2014 | Mccafferty |
| 2015/0022780 A1 | 1/2015 | John et al. |
| 2015/0038893 A1 | 2/2015 | Haffner et al. |
| 2015/0087743 A1 | 3/2015 | Anvar et al. |
| 2015/0148836 A1 | 5/2015 | Heeren |
| 2015/0223984 A1 | 8/2015 | Schieber et al. |
| 2015/0257874 A1 | 9/2015 | Hildebrand et al. |
| 2016/0058552 A1 | 3/2016 | Argal et al. |
| 2016/0058553 A1 | 3/2016 | Salahieh et al. |
| 2016/0128826 A1 | 5/2016 | Silvestrini et al. |
| 2016/0262875 A1 | 9/2016 | Smith et al. |
| 2017/0127941 A1 | 5/2017 | Ostermeier et al. |
| 2017/0164831 A1 | 6/2017 | Choo et al. |
| 2017/0172794 A1 | 6/2017 | Varner et al. |
| 2017/0172799 A1 | 6/2017 | Horvath |
| 2017/0172800 A1 | 6/2017 | Romoda et al. |
| 2017/0181850 A1 | 6/2017 | De Juan et al. |
| 2017/0239272 A1 | 8/2017 | Ambati et al. |
| 2017/0258581 A1 | 9/2017 | Borja et al. |
| 2018/0147051 A1 | 5/2018 | Scholl et al. |
| 2018/0318066 A1 | 11/2018 | Campin et al. |
| 2019/0076243 A1 | 3/2019 | Hadba et al. |
| 2019/0240004 A9 | 8/2019 | Smiley et al. |
| 2019/0269500 A1 | 9/2019 | De Juan et al. |
| 2019/0343679 A1 | 11/2019 | Wardle et al. |
| 2019/0361231 A1 | 11/2019 | Kurz |
| 2019/0374333 A1 | 12/2019 | Shadduck |
| 2020/0000577 A1 | 1/2020 | Smiley et al. |
| 2020/0085620 A1 | 3/2020 | Euteneuer et al. |
| 2020/0246134 A1 | 8/2020 | Hajela et al. |
| 2020/0261266 A1 | 8/2020 | Bley et al. |
| 2021/0100650 A1 | 4/2021 | Smiley et al. |
| 2021/0100652 A1 | 4/2021 | Walz et al. |
| 2023/0089016 A1 | 3/2023 | Noda et al. |

FOREIGN PATENT DOCUMENTS

| | | |
|---|---|---|
| CN | 1378440 | 11/2002 |
| CN | 1384727 | 12/2002 |
| CN | 101039635 | 9/2007 |
| CN | 101277659 | 10/2008 |
| CN | 100471898 C * | 3/2009 |
| CN | 101547958 | 9/2009 |
| CN | 102271622 | 12/2011 |
| DE | 102010010430 | 9/2011 |
| EP | 0898972 | 3/1999 |
| EP | 2060243 | 5/2009 |
| EP | 2192934 | 6/2010 |
| FR | 2655841 | 6/1991 |
| FR | 2784575 | 12/2000 |
| JP | 05-043699 | 2/1993 |
| JP | 07-044538 | 5/1995 |
| JP | 08-034855 | 2/1996 |
| JP | 08-239479 | 9/1996 |
| JP | 09-165449 | 6/1997 |
| JP | 09-294754 | 11/1997 |
| JP | 10-206609 | 8/1998 |
| JP | 11-276509 | 10/1999 |
| JP | 2008-307394 | 12/2008 |
| RU | 1810052 | 4/1993 |
| WO | WO 1995/002378 | 1/1995 |
| WO | WO 1997/006751 | 2/1997 |
| WO | WO 2000/041650 | 7/2000 |
| WO | WO 2000/064655 | 11/2000 |
| WO | WO 2001/060286 | 8/2001 |
| WO | WO 2001/089435 | 11/2001 |
| WO | WO 2001/097742 | 12/2001 |
| WO | WO 2002/051338 | 7/2002 |
| WO | WO 2004/010895 | 2/2004 |
| WO | WO 2004/046768 | 6/2004 |
| WO | WO 2004/072689 | 8/2004 |
| WO | WO 2005/018504 | 3/2005 |
| WO | WO 2005/084588 | 9/2005 |
| WO | WO 2006/004707 | 1/2006 |
| WO | WO 2006/047383 | 5/2006 |
| WO | WO 2006/088440 | 8/2006 |
| WO | WO 2007/005529 | 1/2007 |
| WO | WO 2007/005692 | 1/2007 |
| WO | WO 2007/030095 | 3/2007 |
| WO | WO 2007/061688 | 5/2007 |
| WO | WO 2007/128423 | 11/2007 |
| WO | WO 2007/138564 | 12/2007 |
| WO | WO 2009/015161 | 1/2009 |
| WO | WO 2009/100322 | 8/2009 |
| WO | WO 2009/154455 | 12/2009 |
| WO | WO 2011/106435 | 9/2011 |
| WO | WO 2011/119334 | 9/2011 |
| WO | WO 2012/006186 | 1/2012 |
| WO | WO 2013/142323 | 9/2013 |

OTHER PUBLICATIONS

Baughman et al. "Negative poisson's ratios for extreme states of matter," *Science*, vol. 288, pp. 2018-2022, Jun. 16, 2000.

Baughman, "Avoiding the shrink," *Nature*, vol. 425, pp. 667, Oct. 16, 2003.

Conlisk, A. T. et al. "Mass Transfer and Flow in Electrically Charged Micro- and Nano-channels," *Analytical Chemistry*, vol. 74; iss. 9; pp. 2139-2150; May 2002.

(56) References Cited

OTHER PUBLICATIONS

Dubbelman et al. "The Thickness of the Aging Human Lens Obtained from Corrected Scheimpflug Images," *Optometry & Vision Science*; vo. 78; iss. 6; pp. 411-416; Jun. 2001.

Gorder, P. F.; Electricity can pump medicine in implanted medical devices; Ohio State Research News; 3 pgs.; May 2, 2002 (printed from internet Aug. 19, 2010).

Gordon, "Applications of shape memory polyurethanes," *Proceedings of the First Intl Conf. on Shape Memory and Superelastic Tech.*, Asilomar Conference Center, Pacific Grove, CA, USA, pp. 115-120, Mar. 1994.

Gruber et al. "Exhaustive soxhlet extraction for the complete removal of residual compounds," *Journal of Biomedical Materials Research*, vol. 53; No. 5; pp. 445-448; Mar. 2000.

Jeon et al., "Shape memory and nanostructure in poly(norbornyl-POSS) copolymers," *Polymer International*, vol. 49, pp. 453-457, May 2000.

Kim et al., "Polyurethanes having shape memory effects," *Polymer*, vol. 37, No. 26, pp. 5781-5793, Dec. 1996.

Lakes et al., "Dramatically stiffer elastic composite materials due to negative stiffness phase?," *Journal of the Mechanics and Physics of Solids*, vol. 50, pp. 979-1009, May 2002.

Lakes et al., "Extreme damping in composite materials with negative-stiffness inclusions," *Nature*, vol. 410, pp. 565-567, Mar. 29, 2001.

Lakes et al., "Microbuckling instability in elastomeric cellular sollids," *J. Materials Science*, vol. 28, pp. 4667-4672, Jan. 1993.

Lakes, "A broader view of membranes," *Nature*, vol. 414, pp. 503-504, Nov. 29, 2001.

Lakes, "Deformations in extreme matter," *Science*; perspectives; vol. 288; No. 5473; pp. 1976-1977; Jun. 16, 2000.

Lakes, "Extreme damping in compliant composites with a negative-stiffness phase," *Philosophical Magazine Letters*, vol. 81, No. 2, pp. 95-100, Feb. 2001.

Lakes, "Extreme damping in composite materials with a negative stiffness phase," *Physical Review Letters*, vol. 86, No. 13, pp. 2897-2900, Mar. 26, 2001.

Lakes, "Negative poisson's ratio materials," *Science*, vol. 238, pp. 551, Oct. 23, 1987.

Lakes, "No contractile obligations," *Nature*, vol. 358, pp. 713-714, Dec. 31, 1992.

Langenbucher et al., "Computerized calculation scheme for toric intraocular lenses," *Acta Ophthalmologica Scandinavica*, vol. 82, No. 3, pp. 270-276, Jun. 2004.

Lendlein et al., "Biodegradable, elastic shape-memory polymers for potential biomedical applications", *Science*; vol. 296; pp. 1673-1676; May 31, 2002.

Lendlein et al., "Shape-memory polymers," *Angew. Chem. Int. Ed.*; vol. 41; pp. 2034-2057; Jun. 2002.

Li et al., "Crystallinity and morphology of segmented polyurethanes with different soft-segment length," *Journal of Applied Polymer Science*, vol. 62, pp. 631-638, Oct. 1996.

Liu et al., "Thermomechanical characterization of a tailored series of shape memory polymers," *Journal of Applied Medical Polymers*, vol. 6, No. 2, Dec. 2002.

Mather et al., "Strain recovery in POSS hybrid thermoplastics," *Polymer Preprints*, vol. 41, No. 1, pp. 528-529, Feb. 2000.

Metcalfe et al., "Cold hibernated elastic memory foams for endovascular interventions," *Biomaterials*, vol. 24, pp. 491-497, Feb. 2003.

Qiao et al., Bio-inspired accommodating fluidic intraocular lens; *Optics Letters*; vol. 34; No. 20; pp. 3214-3216; Oct. 15, 2009.

Rosales et al., Pentacam Scheimpflug Quantitativelmaging of the Crystalline Lens andIntraocular Lens; *J. Refractive Surgery*; vol. 25; pp. 421-428; May 2009.

Takahashi et al., "Structure and properties of shape-memory polyurethane block copolymers," *Journal of Applied Polymer Science*, vol. 60, pp. 1061-1069, May 1996.

Tehrani et al. "Capsule measuring ring to predict capsular bag diameter and follow its course after foldable intraocular lens implantation," *J Cataract Refract Surg.*; vol. 29; No. 11; pp. 2127-2134; Nov. 29, 2003.

Tobushi et al., "Thermomechanical properties of shape memory polymers of polyurethane series and their applications," *Journal de Physique IV, Colloque C1*, vol. 6, pp. 377-384, Aug. 1996.

Vass et al. "Prediction of pseudophakic capsular bag diameter based on biometric variables," *J Cataract Refract Surg.*; vol. 25; pp. 1376-1381; Oct. 1999.

Wang et al., "Deformation of extreme viscoelastic metals and composites," *Materials Science and Enginerring A*, vol. 370, pp. 41-49, Apr. 15, 2004.

Wang et al., "Extreme stiffness systems due to negative stiffness elements," *American Journal of Physics*, vol. 72, No. 1, pp. 40-50, Jan. 2004.

Wang et al., "Stable extremely-high-damping discrete viscoelastic systems due to native stiffness elements," *Applied Physics Letters*, vol. 84, No. 22, pp. 4451-4453, May 31, 2004.

Wyant et al.; "Basic Wavefront Aberration Theory for Optical Metrology," *Applied Optics and Optical Engineering*, vol. XI, pp. 1, 28-39, Aug. 10, 1992.

Xu et al., "Making negative poisson's ratio microstructures by soft lithography," *Advanced Materials*, vol. 11, No. 14, pp. 1186-1189, Jun. 1999.

Zhao, H. et al., "The effect of chromatic dispersion on pseudophakic optical performance," *Br J Opthalmol*, vol. 91, pp. 1225-1229, May 2, 2007.

\* cited by examiner

FLUID FOR ACCOMMODATING INTRAOCULAR LENSES

CROSS-REFERENCE TO RELATED APPLICATIONS

This application is a divisional of U.S. application Ser. No. 17/200,047, filed Mar. 12, 2021, now U.S. Pat. No. 11,737,862, which is a continuation of U.S. application Ser. No. 14/555,001, filed Nov. 26, 2014, now U.S. Pat. No. 10,980,629, which is a continuation of U.S. application Ser. No. 13/033,474, filed Feb. 23, 2011, now U.S. Pat. No. 8,900,298, which application claims the benefit of U.S. Provisional Patent Application No. 61/307,354, filed Feb. 23, 2010, the disclosures of which are incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Intraocular lenses ("IOL") may comprise one or more fluids disposed therein. For example, some accommodating IOLs use fluid movement within the IOL, or a change in fluid pressure within the IOL, to effect optical power change in the IOL. Exemplary accommodating IOLs that include a fluid can be found in U.S. Pat. App. Pub. Nos. 2008/0306588, filed Jul. 22, 2008, and 2008/0306587, filed Jul. 22, 2008, the disclosures of which are incorporated herein by reference. Exemplary methods of accommodation in response to natural ciliary muscle movement are also described therein. For example, in the embodiment shown in FIGS. 3-5 in U.S. Pat. App. Pub. No. 2008/0306588, a fluid pressure increase in the optic portion causes the shape of the anterior surface of the optic portion to change, thereby changing the power of the lens. Silicone oil is an example of a fluid that can be used in an IOL. In the embodiment shown, the peripheral portion is in fluid communication with the optic portion, allowing, for example, silicone oil to flow between the optic portion and the peripheral portion. The bulk material of the lens includes anterior lens element 16, intermediate layer 18, and posterior element 22. The bulk material can also be considered to include the haptic bulk material in the peripheral portion of the IOL.

When fluids such as silicone oil are used in an accommodating intraocular lens, the fluid, over time, may tend to swell into the bulk material. This can reduce the amount of silicone oil available to drive the optical power change in the IOL. It is therefore desirable to minimize the amount of swelling into the bulk material. It may also be important to provide silicone oil that does not reduce the response time of the accommodating IOL.

Some IOLs rely on, or can benefit from, a substantially uniform refractive index throughout the IOL. It may therefore also be beneficial to provide silicone oil that has a refractive index that is as close to the refractive index of the bulk material as possible.

Improved fluids (e.g., silicone oils), their methods of manufacture, and their methods of use in accommodating intraocular lenses are therefore needed.

SUMMARY

One aspect of the disclosure is a method of manufacturing silicone oil for use in an intraocular lens, comprising purifying silicone oil to be used in an intraocular lens, wherein the silicone oil has a polydispersity index of less than about 1.5, and in some embodiments less than about 1.3. The silicone oil can have a mean molecular weight of between about 5000 Daltons and about 6500 Daltons. In some embodiments there is no more than about 50 ppm of any low molecular weight component, such as components that have a molecular weight of about 1000 Daltons or less, in the silicone oil to be used in the intraocular lens. In some embodiments the method includes controlling the refractive index of the silicone oil to be between about 1.47 and about 1.49. In some embodiments purification step is a supercritical $CO_2$ extraction, while in some embodiments it is a wiped-film extraction. The purification step substantially prevents the silicone oil from swelling in a bulk polymeric material of the intraocular lens. In some embodiments the silicone oil comprises diphenyl siloxane and dimethyl siloxane, and in some particular embodiments there is about 20% diphenyl siloxane and about 80% dimethyl siloxane.

One aspect of the disclosure is a method of manufacturing silicone oil for use in an intraocular lens, comprising synthesizing silicone oil to be used in an intraocular lens, wherein the silicone oil has a polydispersity index of less than about 1.5. The synthesis can be a living polymerization synthesis. The method also includes a purification step after the synthesis step, which can be, for example, a supercritical $CO_2$ extraction or a wiped-film purification step. In some embodiments the silicone oil has a mean molecular weight of between about 5000 Daltons and about 6500 Daltons. In some embodiments there is no more than about 50 ppm of any low molecular weight component in the silicone oil. In some embodiments the viscosity of the silicone oil is less than about 1000 cSt at about 25° C.

One aspect of the disclosure is a method of manufacturing silicone oil for use in an intraocular lens, comprising purifying silicone oil to be used in an intraocular lens, wherein the silicone oil has a mean molecular weight between about 5000 Daltons and about 6500 Daltons. The silicone oil can have a polydispersity index of less than about 1.5. In some embodiments there is no more than about 50 ppm of any low molecular weight component in the silicone oil. The manufactured silicone oil is adapted to avoid swelling in a bulk polymeric material of the intraocular lens. The silicone oil can comprise diphenyl siloxane and dimethyl siloxane.

One aspect of the disclosure is a method of manufacturing an intraocular lens, comprising providing a silicone oil that has been purified to have a polydispersity index of less than about 1.5; and assembling a bulk polymer material and the silicone oil to form an intraocular lens. The assembling step can comprise advancing the silicone oil into a fluid chamber within the bulk material of the intraocular lens. The silicone oil can have been purified to have a mean molecular weight between about 5000 Daltons and about 6500 Daltons. The silicone oil can have been purified such that there is no more than 50 ppm of any component that has a molecular weight of about 1000 Daltons or less. In some embodiments the silicone oil has been substantially index-matched to at least a portion of the bulk material.

One aspect of the disclosure is a method of using an intraocular lens: comprising creating an opening in the eye; and implanting in a posterior chamber of an eye an intraocular lens comprising silicone oil purified to have a polydispersity index of less than about 1.5.

One aspect of the disclosure is silicone oil adapted to be used in an intraocular lens, wherein the silicone oil has been purified and has a polydispersity index less than about 1.5. The silicone oil can comprise diphenyl siloxane and dimethyl siloxane, and in some embodiments the silicone oil comprises about 20 mol % diphenyl siloxane and about 80% dimethyl siloxane. The silicone oil can have a mean molecular weight between about 5000 Daltons and about 6500 Daltons, and there are no more than 50 ppm of any component that has a molecular weight of about 1000 Daltons or less. In some embodiments the silicone oil has a viscosity of less than about 1000 cSt at about 25° C. The refractive index can be between about 1.47 and about 1.49.

One aspect of the disclosure is silicone oil adapted to be used in an intraocular lens, wherein the silicone oil has been synthesized and has a polydispersity index less than about 1.5.

One aspect of the disclosure is an accommodating intraocular lens comprising a bulk polymeric material and silicone oil that has a polydispersity index less than about 1.5. The silicone oil can have an index of refraction between about 1.47 and about 1.49. The silicone oil can comprise diphenyl siloxane and dimethyl siloxane. The silicone oil can have a mean molecular weight number average of between about 5000 Daltons to about 6500 Daltons. The viscosity of the oil can be less than about 1000 cSt at about 25° C. In some embodiments there is no more than 50 ppm of any component that has a molecular weight of about 1000 Daltons or less.

DETAILED DESCRIPTION

The disclosure herein generally relates to fluid, such as silicone oil, that is used in an intraocular lens. In some embodiments the silicone oil is used in an accommodating intraocular lens that uses fluid movement to effect optical power change in the IOL. The silicone oil can, however, be used in non-accommodating intraocular lenses as well.

Accommodating IOLs can utilize the eye's natural ciliary muscle movements to provide accommodation in the IOL. For example, some accommodating IOLs are implanted within a patient's capsular bag (after the native lens has been removed) and respond to capsular bag reshaping to change the power of the lens. Some IOLs are designed to be implanted outside of the lens capsule and accommodate in other ways. Whatever the method of accommodation, silicone oil disposed within an accommodating IOL can be adapted to be moved within the IOL in response to the eye's natural movement in order to change the lens power. Properties of the silicone oil can therefore affect the accommodative response time of the IOL. The selected silicone oil therefore does not undesirably hinder the response time of the IOL.

When silicone oil is used in accommodating IOL with a bulk material such as a polymeric material, some of the oil components can pass into the bulk material, causing the bulk material to swell. The selected silicone oil or oils therefore avoids the undesirable swelling of the bulk polymer. Exemplary polymeric materials that can be used for the bulk material of the IOL can be found in U.S. application Ser. No. 12/177,720, filed Jul. 22, 2008, and in U.S. application Ser. No. 12/034,942, filed Feb. 21, 2008, the disclosures of which are incorporated herein by reference.

One characteristic of silicone oil that helps ensure an adequate response and avoids undesirable swelling is the polydispersity index ("PDI") of the silicone oil to be used in the IOL. PDI is generally a measure of the distribution of molecular mass in a given sample. A relatively low PDI indicates a relatively narrow range of molecular weights. The silicone oils described herein have a PDI less than about 1.5, and more particularly less than about 1.3.

A second characteristic of the silicone oil that helps ensure an adequate response and avoids undesirable swelling is the mean molecular weight of the silicone oil. When high concentrations of relatively low molecular weight components are present in the silicone oil, a greater number of low molecular weight components pass into the bulk material of the IOL causing the swelling of the bulk material. To avoid undesirable swelling, the concentration of relatively low molecular weight components should be minimized. By reducing the concentration of relatively low molecular weight components and maintaining a high concentration of relatively high molecular weight components, fewer low molecular weight components will pass into the bulk polymer material, reducing the amount of swelling that occurs in the bulk material.

The PDI of the silicone oil and the mean molecular weight of the oil are related—by lowering the PDI of the silicone oil while providing silicone oil with high concentrations of relatively high molecular weight components and low concentrations of low molecular weight components, the response of the IOL is maintained (by providing a silicone oil with suitable viscosity) and undesirable swelling is avoided. Additionally, providing silicone oil with a low PDI and very low concentrations of small molecular weight components means that the silicone oil has a molecular weight just large enough to avoid swelling of the polymer.

In some embodiments silicone oil is provided that has a mean molecular weight between about 5000 and about 6500 Daltons, which is large enough to substantially avoid swelling of the bulk polymeric material. This is preferable to the alternative, which is using a higher molecular weight silicone oil which has inherently fewer small molecule components because almost all molecules comprising it are large. High molecular weight silicone oils can have a correspondingly high viscosity, which can reduce the response time of the accommodating IOL.

The silicone oils described herein have a very low concentration of relatively low molecular weight components. The very low molecular weight components are present in an amount less than about 200 ppm of each component, and in some embodiments less than about 100 ppm. In some particular embodiments the very low molecular weight components are present in an amount less than about 50 ppm.

The relatively low molecular weight components include those less than or equal to about 1000 Daltons. For example, in some embodiments the concentration of components less than or equal to about 1000 Daltons is not more than about 50 ppm.

In one particular embodiment, silicone oil is provided in which no more than 20% of the total silicone by weight is comprised of components below about 4000 Daltons; no more than 10% of the total polymer fluid by weight is comprised of components below 3000 Daltons; and no more than 50 ppm of any components below 1000 Daltons.

The estimated molecular weights and polydispersities described herein are relative to polystyrene molecular weights standards.

The silicone oil generally needs to be designed in such a way as to avoid adverse interactions with the surrounding bulk IOL material, such as swelling, fogging, dissolving or reacting with the material (e.g., poly acrylate) in some IOLs. The degree of solubility of the silicone oil in the bulk material is dependent on the chemical structure and molecular weight distribution of the silicone oil. Other parameters that influence this interaction are the composition and properties of the bulk material such as homogeneity, chemical structure, hydrophobicity, modulus, and crosslink density.

The viscosity of the silicone oil also generally needs to be defined and minimized because, in embodiments in which the fluid-driven accommodating IOL operates dynamically, the IOL must have an appropriate response time. In some embodiments the viscosity of the silicone oil is less than about 1000 cSt at 25° C.

In some embodiments the silicone oil is comprised of diphenyl siloxane and dimethyl siloxane. In some embodiments the oil is a diphenyl siloxane and dimethyl siloxane copolymer with about 20 mol % diphenyl siloxane and about 80 mol % dimethyl siloxane.

In some IOLs it may be desirable to avoid creating an optical interface between the bulk material of the IOL and the silicone oil within the IOL. This can be done by index-matching the silicone oil to the bulk material of the IOL, which in some embodiments is a polymeric material. "Index-matching" as used herein refers to minimizing the optical interface between first and second media. For example, index-matching silicone oil and a polymeric material refers to attempting to eliminate an optical interface therebetween, and "substantially the same" refers to indexes of refraction that, even though they may be slightly different, are intended to be as close as possible to minimize the difference in refractive indexes.

In some embodiments in which the silicone oil is index-matched to the bulk polymeric material, the refractive index of silicone oil is between about 1.47 and about 1.53, and in some embodiments is between about 1.47 and about 1.49.

In some embodiments the silicone oil must be able to be filtered through an about 0.7 micron filter. In some embodiments the percent volatiles are less than about 0.2%. In some embodiments the silicone oil has a chromatic dispersion less than or equal to about 0.035 refractive index units in the visible range of 400 nm to 750 nm at 35° C. In some embodiments the silicone oil components are fully miscible with each other without evidence of phase separation (i.e. cloudiness or suspensions). In some embodiments the silicone oil has greater than 85% transmittance in the range of 400 nm to 1100 nm for about a 1 cm thick fluid sample.

In addition, the silicone oil should be clear, colorless, have less than about 10 ppm heavy metals and other insoluble inorganics contaminants, and have substantially no silanols.

Synthesis

The molecular weight, polydispersity, and in some instances the refractive index of the silicone oil can be controlled by the way in which the silicone oil is synthesized and purified. The viscosity of the oil is related to the molecular weight of the oil, the polydispersity of the oil, and the architecture of the bulk polymer, all of which are influenced by the synthesis and purification of the polymer. However, a target viscosity can not be arbitrarily selected independent of the target molecular weight, polydispersity, composition, and architecture of the silicone oil. A general class of polymer synthesis reactions known as "living polymerization reactions" can offer the degree of control necessary to assist in meeting some of the design requirements for a silicone oil.

The term "living polymerization" implies a polymerization reaction that does not have a significant number of chain terminating or chain transferring side reactions. The absence of side reactions allows living polymerizations to be used to synthesize a variety of materials that would be otherwise difficult to prepare. This class of polymerization reactions can be used to prepare polymers with a variety of 1) architectures—including linear, "star", and "comb" polymers; 2) compositions—homopolymers, random copolymers, block copolymers, and graft copolymers; and 3) functionalized polymers—one and two end functional polymers, and side functional polymers. This class of polymerization reactions can be used to prepare polymers that often have a narrow molecular weight distribution and at a variety of molecular weights. As a result, living polymerizations are often employed when polymers with specific structures and compositions are needed. For example, a polymer with a large molecular weight distribution can be considered to be a mixture of a large number of compounds, and the properties of the material are some function of that distribution. Polymers that have a small molecular weight distribution, however, as can result from a living polymerization, can be considered a "purer" sample, with properties that are better defined.

Anionic and cationic living polymerizations have been described in the art. More recently, radical living polymerizations may have been developed. In an example of an anionic synthetic route, the use of alkyl lithium compounds in the ring opening polymerization of cyclotrisiloxanes appears to be a "living" polymerization, allowing for the degree of control needed to make the silicone oils described above. By varying the ratio of phenyl containing cyclotrisiloxanes to methyl only containing cyclotrisiloxanes (that is, preparing a random block copolymer), the refractive index of the silicone oil can be varied between the refractive index of either pure homopolymer alone (i.e., between pure diphenyl polysiloxane and pure dimethyl polysiloxane).

As another example, the refractive index of the silicone oil can be varied by varying the ratio of a tetramethyl-diphenyl-cyclotrisiloxane to hexamethyl cyclotrisiloxanes. Varying this ratio can provide different refractive indexes between about 1.40 and about 1.54, including those between about 1.47 and 1.49.

As mentioned above, a living polymerization also offers the advantage of being able to prepare polymer products of a targeted molecular weight. This can be accomplished by varying the monomer to initiator ratio during the polymerization reaction, an application which can be applied to the preparation of silicone oils of a specified formula weight.

The feature of a narrow range of molecular weight products is also an advantage that can be realized in the preparation of silicone oils because fewer low molecular weight oligomers are made during the polymerization reaction. The smaller quantity of the low molecular weight materials prepared minimizes the amount of purification that needs to occur later to remove them from the higher molecular weight products. For example, when fewer low molecular weight oligomers are made during the polymerization reaction, it is easier to extract the low molecular weight materials when purifying the synthesized silicone oil using a supercritical $CO_2$ extraction (described below), resulting in higher yields of the desired product.

While the viscosity of a polymer is not directly related to the way in which the polymer is prepared, a living polymerization can also be used to indirectly modify this feature of the product polymer. Living polymerizations can be used to make polymer architectures that would be difficult to accomplish using other synthetic strategies. For example, "comb" polymers, "star" polymers, and other branched structures can be prepared, which, even though they have a very similar chemical composition to a "linear" polymer, may have different physical properties (e.g., viscosity), because of the different physical geometries those structures have. Preparation of a highly branched silicone oil may yield a product which has a significantly lower viscosity than a silicone oil with the same molecular weight but a linear structure.

Silicone oils can also be prepared using other synthetic strategies such as the base catalyzed ring opening of cyclotrisiloxanes, and the condensation of dialkyldichloro silanes with water. These synthetic strategies can also prepare silicone oils with many of the characteristics described above, but can require more effort on purification.

Purification

Silicon oils can be purified in a variety of ways. Wiped film evaporation can be used to remove low molecular weight compounds that have a high boiling point. The silicone oil product may, however, be discolored on excessive heating when using wiped film evaporation.

Supercritical $CO_2$ extraction is one exemplary purification method that can be used to selectively remove fractions of silicone oil based on molecular weight and based on chemical affinity. Supercritical $CO_2$ extraction to purify silicone oils to produce silicone vitreoretinal tamponades is described in U.S. Pat. No. 7,276,619, the entire disclosure of which is incorporated by reference herein. These oils are not used for IOLs, are particularly not in fluid-drive accommodating IOLs. Pressure, temperature, rate of extraction conditions, and the use of co-eluting solvents such as, for example, acetone, can be varied to yield fractions that have a narrow molecular weight distribution (i.e., a low PDI). A mixture can be separated in such a way as to strip the very low and very high molecular fractions from a sample achieving the desired molecular weight. Because supercritical extraction conditions can be varied to get separation based on chemical affinity, this purification method can also be used to achieve a desired refractive index. Supercritical $CO_2$ extraction can therefore be used to produce a silicone oil with, for example, an index of refraction substantially the same as a bulk polymer to be used in an intraocular lens (e.g., in a fluid-driven accommodating intraocular lens).

Tables 1-3 provide data from exemplary supercritical $CO_2$ extractions of sample silicone oils.

TABLE 1

| Silicone Oil Sample | Time at 85 C. (Hrs) | % Weight Change |
|---|---|---|
| 1 | 404 | 43.15 |
| 2 | 404 | 24.48 |
| 3 | 404 | 11.11 |
| 4 | 404 | 6.15 |
| 6 | 404 | 1.67 |
| 7 | 404 | 13.25 |

TABLE 2

| Silicone Oil Sample | Mean RI |
|---|---|
| 1 | 1.477792 |
| 2 | 1.48604 |
| 3 | 1.487633 |
| 4 | 1.49067 |
| 5 | 1.494362 |
| 6 | 1.498737 |
| 7 | 1.492858 |

TABLE 3

| Silicone Oil Sample | Viscosity (cP) at 25.0 C. | stdev |
|---|---|---|
| 1 | 38.40 | 1.20 |
| 2 | 87.12 | 1.37 |
| 3 | 175.68 | 2.01 |

Similarly, preparative scale size exclusion chromatography is an alternative method to fractionate a polymer sample into molecular weight components. Fractional precipitation of the silicone oil may also be used to separate components of the product polymer.

Removal of silicone oil components that dissolve into the bulk IOL material over time (e.g., during storage) may also be accomplished by exposing the silicone oil to bulk quantities of the IOL material, or other materials that have been selected for that purpose. On storage with an appropriate material, the components of the silicone oil that dissolve into the bulk IOL polymeric material may be removed by adjusting the ratio of silicone oil to polymer adsorbent so that sufficiently low levels of those materials remain in the oil.

While silicone oils used in accommodating IOLs are primary described herein, it is possible to use any of the silicone oils in a non-accommodating IOL. For example, a non-accommodating IOL can have a relatively rigid outer polymeric shell surrounding a silicone oil core. Swelling of the bulk polymeric material would still need to be taken into consideration, and hence the methods of manufacturing desired silicone oil described herein could be utilized.

What is claimed is:

1. An intraocular lens, comprising:
a fluid chamber, and
a silicone oil disposed in the fluid chamber,
wherein the silicone oil is polymerized as branched polymeric structures.

2. The intraocular lens of claim 1, wherein the silicone oil is polymerized using a living polymerization reaction.

3. The intraocular lens of claim 1, wherein the silicone oil comprises a star-like polymeric structure.

4. The intraocular lens of claim 1, wherein the silicone oil comprises a comb-like polymeric structure.

5. The intraocular lens of claim 1, wherein a refractive index of the silicone oil is substantially the same as the refractive index of a bulk polymeric material of the intraocular lens, wherein the intraocular lens further comprises an optic portion, and wherein the optic portion is made in part of the bulk polymeric material, wherein the fluid chamber is within the optic portion.

6. The intraocular lens of claim 1, wherein the intraocular lens is a fluid-driven accommodating intraocular lens.

7. The intraocular lens of claim 1, wherein the silicone oil has a polydispersity index of less than 1.5.

8. The intraocular lens of claim 1, wherein the silicone oil has a mean molecular weight of between 5000 Daltons and 6500 Daltons.

9. The intraocular lens of claim 1, wherein no more than 20 wt % of the silicone oil is comprised of components below 4000 Daltons.

10. The intraocular lens of claim 1, wherein no more than 10 wt % of the silicone oil is comprised of components below 3000 Daltons.

11. An intraocular lens, comprising:
a fluid chamber, and
a silicone oil disposed in the fluid chamber,
wherein the silicone oil is polymerized as branched polymeric structures, and wherein the branched polymeric structures comprise an X-shaped polymeric structure.

12. An intraocular lens, comprising:
a fluid chamber, and
a silicone oil disposed in the fluid chamber,
   wherein the silicone oil is polymerized as branched polymeric structures, and wherein the intraocular lens is a non-accommodating intraocular lens.

\* \* \* \* \*